(12) United States Patent
Stein et al.

(10) Patent No.: US 11,517,292 B2
(45) Date of Patent: Dec. 6, 2022

(54) SYSTEM AND A METHOD FOR NON-INVASIVE MONITORING OF ESTROGEN

(71) Applicant: AVA AG, Zürich (CH)

(72) Inventors: Peter Stein, Zürich (CH); Brigitte Leeners, Uster (CH)

(73) Assignee: FEMTEC HEALTH, INC., Houston, TX (US)

( * ) Notice: Subject to any disclaimer, the term of this patent is extended or adjusted under 35 U.S.C. 154(b) by 851 days.

(21) Appl. No.: 16/345,543

(22) PCT Filed: Oct. 26, 2017

(86) PCT No.: PCT/EP2017/077406
§ 371 (c)(1),
(2) Date: Apr. 26, 2019

(87) PCT Pub. No.: WO2018/077998
PCT Pub. Date: May 3, 2018

(65) Prior Publication Data
US 2019/0307430 A1    Oct. 10, 2019

(30) Foreign Application Priority Data
Oct. 27, 2016 (CH) .................................... 01440/16

(51) Int. Cl.
*A61B 5/00* (2006.01)
*A61B 10/00* (2006.01)
(Continued)

(52) U.S. Cl.
CPC ........ *A61B 10/0012* (2013.01); *A61B 5/0205* (2013.01); *A61B 5/1118* (2013.01);
(Continued)

(58) Field of Classification Search
CPC . A61B 10/0012; A61B 5/0205; A61B 5/1118; A61B 5/43; A61B 5/4306;
(Continued)

(56) References Cited

U.S. PATENT DOCUMENTS 3,986,494 A * 10/1976 Preti ................... A61B 10/0012
422/50
4,541,439 A    9/1985 Hon
(Continued)

FOREIGN PATENT DOCUMENTS

| EP | 0132119 A2 | 1/1985 |
|---|---|---|
| WO | WO 2016/102971 A2 | 6/2016 |
| WO | WO 2016/131630 A1 | 8/2016 |

OTHER PUBLICATIONS

International Search Report for Swiss Application No. CH 14402016, dated Feb. 20, 2017, in 4 pages.
(Continued)

*Primary Examiner* — May A Abouelela
(74) *Attorney, Agent, or Firm* — Knobbe, Martens, Olson & Bear, LLP (57) ABSTRACT

An electronic system for non-invasive monitoring of estrogen of a female human comprises a wearable device (1) and a processor (13, 30, 40). The wearable device (1) includes a first sensor system (101) configured to be worn in contact with the skin of the female human and to determine a level of perfusion of the female human. The processor (13, 30, 40) is configured to receive and store the level of perfusion of the female human from the first sensor system (101) for a respective point in time. The processor (13, 30, 40) is further configured to determine a change in the level of perfusion of the female human, using the levels of perfusion of the female human stored for a plurality of respective points in time. Furthermore, the processor (13, 30, 40) is configured
(Continued)

to detect a change in estrogen level of the female human based on the change in the level of perfusion of the female human.

14 Claims, 6 Drawing Sheets

(51) Int. Cl.
    *A61B 5/11*     (2006.01)
    *A61B 5/0205*     (2006.01)
    *A61D 17/00*     (2006.01)
    *A61B 5/026*     (2006.01)
    *A61B 5/01*     (2006.01)

(52) U.S. Cl.
    CPC .............. *A61B 5/43* (2013.01); *A61B 5/4306* (2013.01); *A61B 5/681* (2013.01); *A61B 5/7239* (2013.01); *A61D 17/002* (2013.01); *A61B 5/01* (2013.01); *A61B 5/026* (2013.01); *A61B 2010/0016* (2013.01); *A61B 2010/0019* (2013.01)

(58) Field of Classification Search
    CPC ......... A61B 5/681; A61B 5/7239; A61B 5/01; A61B 5/026; A61B 2010/0016; A61B 2010/0019; A61D 17/002
    USPC ......................................................... 600/551
    See application file for complete search history.

(56) References Cited

U.S. PATENT DOCUMENTS

| | | | | |
|---|---|---|---|---|
| 4,836,216 A * | 6/1989 | Fernando | ........... | A61B 10/0012 600/551 |
| 7,977,103 B2 * | 7/2011 | Martin | ............... | A61B 10/0012 436/63 |
| 8,420,398 B2 * | 4/2013 | Goldman | ............... | A61D 19/02 600/35 |
| 9,867,597 B1 * | 1/2018 | Buard | ................ | A61B 5/02438 |
| 2004/0181167 A1 * | 9/2004 | Carney | .................... | A61B 5/42 435/7.1 |
| 2005/0010128 A1 * | 1/2005 | Shiraishi | ................ | G01N 33/76 600/551 |
| 2007/0100666 A1 * | 5/2007 | Stivoric | ................ | A63F 13/211 374/E1.002 |
| 2008/0214949 A1 | 9/2008 | Stivoric et al. | | |
| 2008/0228058 A1 * | 9/2008 | Cinti | .................... | A61D 17/002 600/551 |
| 2008/0255472 A1 * | 10/2008 | Kuo | .................... | A61B 10/0012 382/128 |
| 2008/0311047 A1 * | 12/2008 | Kaper | .................. | C07K 14/245 435/254.2 |
| 2010/0036279 A1 * | 2/2010 | Rieth | .................. | A61B 5/14539 600/551 |
| 2010/0274073 A1 * | 10/2010 | Regas | .................. | A61D 17/002 600/35 |
| 2010/0312137 A1 * | 12/2010 | Gilmour | .............. | G01N 33/558 600/551 |
| 2013/0338531 A1 * | 12/2013 | Regas | .................. | A61D 17/002 600/551 |
| 2016/0066894 A1 | 3/2016 | Barton-Sweeney | | |
| 2016/0270768 A1 * | 9/2016 | Kersken | ............ | A61B 10/0012 |
| 2017/0071581 A1 * | 3/2017 | Sacks | ................ | A61B 10/0012 |
| 2017/0202185 A1 * | 7/2017 | Trumbull | ............ | A61B 15/14507 |
| 2017/0235443 A1 * | 8/2017 | Suzuki | .................... | G16H 10/20 715/780 |
| 2017/0258455 A1 * | 9/2017 | Qi | ........................ | A61B 5/4306 |
| 2017/0347632 A1 * | 12/2017 | Auer | .................... | A01K 11/006 |
| 2018/0055490 A1 * | 3/2018 | Lee | .................... | A61B 10/0012 |
| 2018/0214028 A1 * | 8/2018 | Zhang | ................ | A61B 5/4318 |
| 2018/0228474 A1 * | 8/2018 | Suzuki | .............. | A61B 10/0012 |
| 2018/0368814 A1 * | 12/2018 | R. Kudtarkar | ....... | A61B 5/4318 |
| 2019/0110692 A1 * | 4/2019 | Pardey | .................... | A61B 5/01 |

OTHER PUBLICATIONS

International Search Report and Written Opinion of the International Searching Authority for International Application No. PCT/EP2017/077406, dated Feb. 7, 2018, in 13 pages.

* cited by examiner

SYSTEM AND A METHOD FOR NON-INVASIVE MONITORING OF ESTROGEN

CROSS-REFERENCE TO RELATED APPLICATIONS

This application is the U.S. National Phase under 35 U.S.C. § 371 of International Application PCT/EP2017/077406, filed Oct. 26, 2017, which claims priority to CH Application No. 01440/16, filed Oct. 27, 2016.

FIELD OF THE INVENTION

The present invention relates to system and method for non-invasive monitoring of estrogen. Specifically, the present invention relates to an electronic system and a method for non-invasive monitoring of estrogen of a female human, using a wearable device with sensor systems for measuring physiological parameters of the female human.

BACKGROUND OF THE INVENTION

Since the introduction of the contraceptive pill in 1960, decades have passed without major developments in the birth control market. Within the last years, so called fertility apps for mobile devices were becoming attractive for an increasing number of women. These applications use the calendar method for determining fertile time periods. Nevertheless, most non-hormonal birth control tools, such as these apps or the well-known temperature method, are found cumbersome and unreliable by many women. Generally, by relying on more than one physiological parameter the reliability can be increased significantly for determining the fertility phase of a female in connection with non-hormonal birth control. For example, the so-called symptothermal method uses a combined analysis of cervical mucus and temperature measurements for determining the fertile and infertile days of a woman. While this yields a better reliability, it is typically found complicated and very cumbersome by women.

WO 97/22298 describes an apparatus with a microprocessor that processes data from wrist worn sensors measuring eccrine sweat to observe the pattern in pH change during the menstrual cycle for determining the fertility status of a female.

CN 2033149470 describes a multifunctional watch that comprises a microprocessor and a temperature sensor for monitoring the menstrual cycle of a female.

WO 2016/131630 describes a wearable device which identifies the fertile phase based on physiological parameters. WO 2016/131630 does not describe or provide any reference to calculating hormonal variations.

EP 0132119 describes a device employing plethysmographic measurement to determine the blood flow reaction in response to a stimulus. EP 0132119 does not describe or provide any reference to using or relying on parameters other than those calculated from the blood flow.

US 2016/066894 mentions that multiple parameters measured with various sensors can be used to monitor varying hormonal levels. US 2016/066894 does not describe or provide any reference on how these parameters are used.

US 2004/081024 describes another wristwatch that comprises a temperature sensor and a computing device for predicting the ovulation phase.

US 2014/246500 mentions that ovulation can be detected with wrist based collected data. US 2014/246500 does neither describe how to process the collected data, nor make it possible to predict ovulation and to determine in advance the fertile phase which would be valuable for women who want to become pregnant.

WO 2015/150434 describes an unobtrusive ovulation tracking system using a subject's heart rate. The time of ovulation is considered a particularly fertile time. According to WO 2015/150434, the likelihood of ovulation is predicted based on heart rate variability features extracted from the heart rate. While heart rate variability is useful as an indicator for ovulation, its reliability is affected by various external influences such as drugs, e.g. alcohol or caffeine, or stress, etc.

The level of estrogen could also be used as an indicator or predictor of ovulation. The estrogen level is measured from blood serum or urinary metabolites (E3G). Using blood serum for determining estrogen level is advantageous in that it provides a direct measurement of the concentration of estrogen that is actually delivered to the brain. However, the blood serum can only be obtained invasively, e.g. through venipuncture. Moreover, there is a substantial time lag between taking a blood sample and obtaining the test results from processing at a laboratory. The process of determining estrogen levels from blood serum is not only time consuming and inconvenient, but also costly and, thus, not suitable for continuous monitoring. As estrogen is delivered in pulses, measurement uncertainty is increased because an overall picture of estrogen production over time is missing. Determining estrogen levels from urinary metabolites is considerably less invasive than taking blood samples. Taking urine samples is also less costly, if home tests are used, but also less precise. Particularly, because the measurement depends on individual state of hydration status and metabolisation. Determining estrogen levels from urine samples has an inherent time lag of a couple of minutes, for home tests, and a couple of hours, for laboratory tests, before the result is available. Thus, as the blood based approach, determining estrogen levels from urinary metabolites is not practical for continuous monitoring and an overall picture of estrogen production over time is not obtained. It is also to be noted that the concentration of estrogen in urine can differ significantly from concentration in blood.

SUMMARY OF THE INVENTION

It is an object of this invention to provide an electronic system and a method for monitoring estrogen of a female human, which system and method do not have at least some of the disadvantages of the prior art. In particular, it is an object of the present invention to provide an electronic system and a method for non-invasive monitoring estrogen level of a female human.

According to the present invention, these objects are achieved through the features of the independent claims. In addition, further advantageous embodiments follow from the dependent claims and the description.

According to the present invention, the above-mentioned objects are particularly achieved in that an electronic system comprises, for non-invasive monitoring of estrogen of a female human, a wearable device including a sensor system configured to be worn in contact with the skin of the female human and to determine one or more physiological parameters of the female human. The electronic system further comprises a processor configured to receive and store the physiological parameters of the female human from the sensor system for a respective point in time. The processor is further configured to determine a change in the physiological parameters of the female human, using the physiological parameters of the female human stored for a plurality of respective points in time, and to detect a change in estrogen level of the female human based on the change in the physiological parameters of the female human.

This non-invasive monitoring of estrogen makes possible continuous monitoring of the estrogen level, in a highly convenient and efficient fashion, without requiring any inconvenient and costly disposables or time-consuming laboratory analysis. The non-invasive detection of the changes in estrogen level allows for early recognition of a female's fertile phase, based on the onset of estrogen. Even in cases of highly irregular cycles and polycystic ovary syndrome (PCOS), fertile levels can be tracked. The non-invasive estrogen monitoring can be used by women to determine when to take Progesterone serum samples in ART cycles (Assisted Reproductive Techniques). Moreover, the non-invasive estrogen monitoring assists postmenopausal women in monitoring the effectiveness of HRT (Hormonal Replacement Therapies).

In an embodiment, the sensor system is configured to determine a level of perfusion of the female human; and the processor is configured to receive and store the level of perfusion of the female human from the sensor system for a respective point in time, to determine a change in the level of perfusion of the female human, using the levels of perfusion of the female human stored for a plurality of respective points in time; and to detect the change in estrogen level of the female human based on the change in the level of perfusion of the female human.

In an embodiment, the processor is configured to determine the change in the level of perfusion of the female human by calculating a first derivative of a course of the level of perfusion.

In a further embodiment, the processor is configured to determine the change in the level of perfusion of the female human by calculating a first derivative of a course of a perfusion index, the perfusion index being defined by an AC component of the level of perfusion normalized by a DC component of the level of perfusion.

In an embodiment, the processor is configured to determine the change in the level of perfusion of the female human over one or more set time intervals during a resting phase of the female human.

In a further embodiment, the sensor system is configured to determine non-invasively the one or more physiological parameters of the female human, the one or more physiological parameters including a level of perfusion, heart rate variability, heart rate, breathing rate, blood pressure, temperature, and/or bio-impedance.

In a further embodiment, the processor is configured to determine a resting phase of the female human, using the one or more physiological parameters of the female human.

In an embodiment, the processor is configured to receive and store one or more behavioral parameters of the female human from a mobile communication device, the one or more further behavioral parameters including activity level, number of social interactions, number of intercourses, communication style, and/or type of contacts; and the processor is configured to detect the change in estrogen level of the female human, using the one or more behavioral parameters of the female human.

In a further embodiment, the processor is configured to determine a peak of the change in the level of perfusion of the female human during a menstrual cycle of the female human, and to determine a predicted time of ovulation of the female human, using the peak of the change in the level of perfusion.

In an embodiment, the processor is arranged in the wearable device and configured to determine the change in estrogen level of the female human using the physiological parameters measured by the sensor system of the wearable device.

In a further embodiment, the processor is arranged in an external system, separated from the wearable device. The wearable device further comprises a communication module configured to transmit the physiological parameters measured by the sensor system of the wearable device to the external system, and the processor is configured to determine the change in estrogen level of the female human using the physiological parameters received from the wearable device.

In addition to the electronic system, the present invention also relates to a method of non-invasive monitoring of estrogen of a female human. The method comprises: receiving in a processor from a sensor system of a wearable device one or more physiological parameters of the female human for a respective point in time; storing, by the processor, the physiological parameters of the female human for the respective point in time; determining, by the processor, a change in the physiological parameters of the female human, using the physiological parameters of the female human stored for a plurality of respective points in time; and detecting, by the processor, a change in estrogen level of the female human based on the change in the physiological parameters of the female human. In an embodiment, the method further comprises: receiving in the processor from the sensor system of the wearable device the one or more physiological parameters of the female human including a level of perfusion, heart rate variability, heart rate, breathing rate, blood pressure, temperature, and/or bio-impedance.

In addition to an electronic system and a method of non-invasive monitoring of estrogen of a female human, the present invention also relates to a computer program product comprising a non-transient computer-readable medium having stored thereon computer program code configured to control one or more processors of a computerized system. The computer program code is configured to control the one or more processors such that the computerized system performs the steps of: receiving from a sensor system of a wearable device one or more physiological parameters of the female human for a respective point in time; storing the physiological parameters of the female human for the respective point in time; determining a change in the physiological parameters of the female human, using the physiological parameters of the female human stored for a plurality of respective points in time; and detecting a change in estrogen level of the female human based on the change in the physiological parameters of the female human.

In an embodiment, the computer program code is further configured to control the one or more processors of the computerized system, such that the computerized system performs the steps of: receiving from the sensor system of the wearable device the one or more physiological parameters of the female human including a level of perfusion, heart rate variability, heart rate, breathing rate, blood pressure, temperature, and/or bio-impedance.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
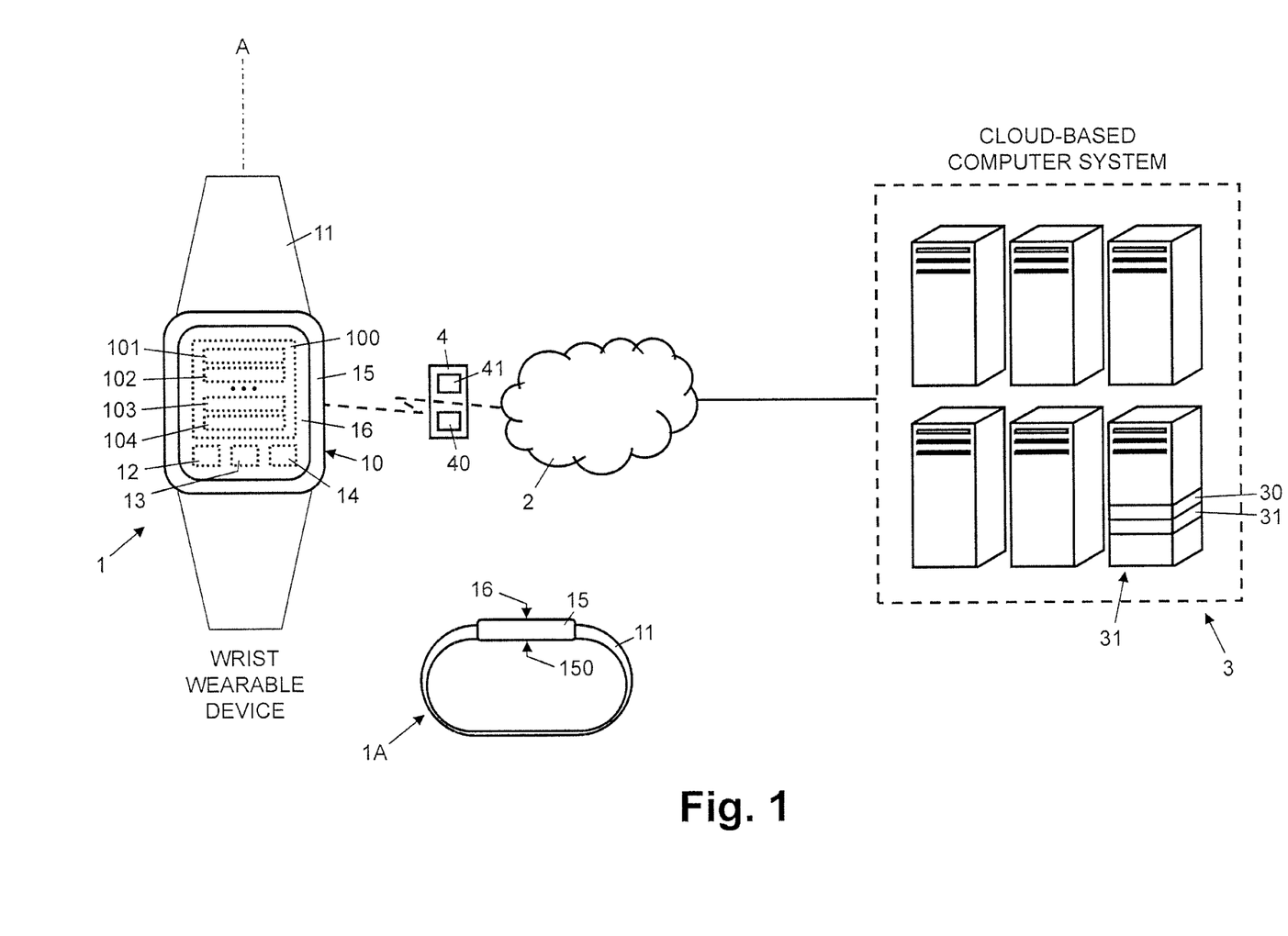
FIG. 1: shows a block diagram illustrating schematically an electronic system for non-invasive monitoring of estrogen of a female human, the system comprising a wearable device and a processor with a processor in the wearable device and/or an external system.

In FIG. 1, reference numeral 3 refers to a computer system, e.g. a cloud-based computer system, comprising one or more computers 31 with one or more processors 30 and a data storage system 31. The computer system 3 or its processors 30, respectively, are connected to the data storage system 31 and configured to execute various functions, as will be explained later in more detail. The data storage system 31 comprises RAM, flash memory, hard disks, data memory, and/or other data stores.

In FIG. 1, reference numeral 4 refers to a mobile communication device, e.g. a cellular telephone or a tablet computer, comprising one or more processors 40 and a data store 41. The processors 40 are connected to the data store 41 and configured to execute various functions, as will be explained later in more detail. The data store comprises RAM, flash memory, data memory, and/or other data storage systems.

In FIG. 1, reference numeral 1 refers to a wearable device, e.g. a wrist wearable device, specifically a wrist wearable electronic device. Reference numeral 1A refers to a cross-sectional view of the wearable device 1 along central axis A. The wearable device 1 includes a fixation system for attaching the wearable device 1 on the body of a user, specifically, for attaching the wearable device 1 in contact with the skin of the user; in the embodiment shown in FIG. 1, the wearable device 1 comprises a wrist band 11 and a device body 10 attached to or integrated in the wrist band 11. The wristband 11 is implemented as a watchstrap, a watchband, a bracelet, or the like. The device body 10 comprises a housing 15 and an optional display 16 integrated in the housing 15.

As illustrated schematically in FIG. 1, wearable device 1 comprises several sensor systems 100, including a perfusion sensor system 101 configured to measure the level of perfusion, i.e. the passage or flow of blood through the blood vessels, specifically the level of skin perfusion of the female user.

The sensor systems 100 further include a bio-impedance sensor system 102 with an electrical resistance or conductance measuring system for measuring bio-impedance of the female user based on the galvanic skin response.

The sensor systems 100 further include a sensor system 103 with optical sensors 103 configured to generate photoplethysmography (PPG) signals for measuring heart rate and heart rate variability. For example, sensor system 103 comprises a PPG-based sensor system for measuring heart rate and heart rate variability as described in Simon Arberet et al., "Photoplethysmography-Based Ambulatory Heartbeat Monitoring Embedded into a Dedicated Bracelet", Computing in Cardiology 2013; 40:935-938, included herewith by reference in its entirety.

The sensor systems 100 further includes a sensor system 104 with one or more accelerometers for measuring body movements (acceleration). In an embodiment, for the purpose of detecting resting, particularly sleep phases, the accelerometers are implemented in combination with the PPG-based sensor system, as described in Philippe Renevey et al., "PHOTOPLETHYSMOGRAPHY-BASED BRACELET FOR AUTOMATIC SLEEP STAGES CLASSIFICATION: PRELIMINARY RESULTS", IASTED 2014, Zurich, Switzerland, included herewith by reference in its entirety.

The sensor systems 100 further include a temperature sensor system 105 for measuring the user's temperature; specifically, the user's skin temperature; more specifically, the wrist's skin temperature. The temperature sensor system 105 comprises one or more sensors, including at least one temperature sensor.

The perfusion sensor system 101, bio-impedance sensor system 102, the optical sensors 103, and the temperature sensor system 105 are integrated in the housing 15 of the wearable device 1 and are arranged on a rear side 150 of the wearable device 1, e.g. opposite of the optional display 16, facing the user's skin in a mounted state of the wearable device 1. In the mounted state when the device 1 is actually attached and worn, e.g. on the wrist, just as one would wear a watch, the rear side 150 of the wearable device 1 or the rear side 150 of its housing 15, respectively, is in contact with the skin, e.g. the skin of the wrist, i.e. the perfusion sensor system 101, the bio-impedance sensor system 102, the optical sensors 103, and the temperature sensor system 105 touch the skin or at least face the skin, e.g. the skin of the wrist. The wearable device 1 further comprises a data store 12, e.g. data memory such as RAM or flush memory, and an operational processor 13 connected to the data store 12 and the sensor systems 100. The processor 13 comprises an electronic circuit configured to perform various functions that will be described later in more detail.

As illustrated in FIG. 1, in an embodiment, the wearable device 1 further comprises a communication module 14 connected to the processor 13. The communication module 14 is configured for data communication with an external system 3, 4, that is separated from the wearable device 1, i.e. a computerized system that is arranged in a different housing than the wearable device 1. Depending on the embodiment and/or configuration, the external system is a remote computer system 3 or a mobile communication device 4. Accordingly, the communication module 14 is configured for data communication with the remote computer system 3 via a network 2 and/or with the mobile communication device 4 via a close range communication interface. The network 2 comprises a mobile radio network such as a GSM-network (Global System for Mobile communication), a UMTS-network (Universal Mobile Telephone System), or another mobile radio telephone system, a wireless local area network (WLAN), and/or the Internet. For example, for close range communication, the communication module 14 comprises a Bluetooth communication module, e.g. a Low Energy Bluetooth module, an RFID (Radio Frequency Identifier) communication module, e.g. an NFC (Near Field Communication) module, or another close range communication module configured for direct data communication with the external mobile communication device 4. In an alternative embodiment, the mobile communication device 4 is configured to facilitate the data communication between the wearable device 1 and the remote computer system 3, e.g. by relaying the measurement data from the wearable device 1 via the network 2 to the remote computer system 3, for processing. Although not illustrated, the wearable device 1 further comprises a timer module configured to generate current time and date information, e.g. a clock circuit or a programmed timer module. The timer module is further configured to generate time stamps including the current time and date.

Figure 2:
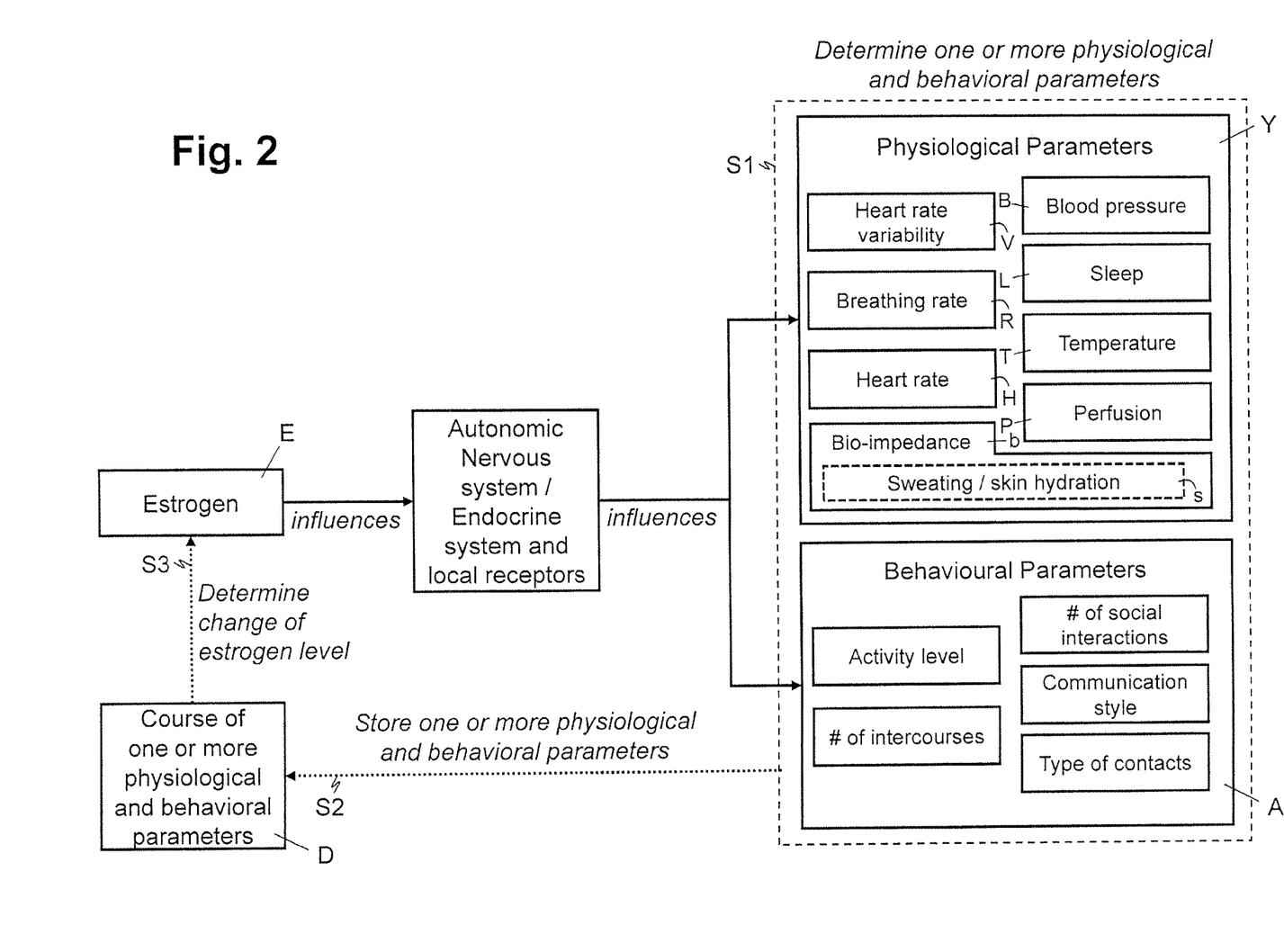
FIG. 2: shows a flow diagram illustrating schematically an exemplary sequence of steps for non-invasive monitoring of estrogen of a female human by determining and analyzing one or more physiological parameters of the female human.

As illustrated schematically in FIG. 2, the estrogen E influences the autonomous nervous system, the endocrine system, and local receptors of a (female) human. Likewise the autonomous nervous system, the endocrine system, and local receptors of a (female) human influence physiological parameters Y and the behavior and related behavioral parameters A of the female human.

In the following paragraphs, the functions executed by the processor 13 of the wearable device 1 and/or the processor(s) 30, 40 of the computer system 3 and/or the mobile communication device 4 are described with reference to FIG. 2. Specifically, described are the functions executed by these processors 13, 30, 40 for non-invasive monitoring of estrogen E of a female human and non-invasive detection of a change in estrogen level E of the female human.

In step S1, physiological parameters Y of the female human are measured by way of the wearable device 1. Preferably, the measurements of the various physiological parameters Y of the female user are performed concurrently. The measurements are performed periodically. In an embodiment, the periodic measurements for monitoring and determining changes in estrogen levels CE are limited to specific time intervals, e.g. during night time or, more specifically, during the sleep phase with resting pulse, e.g. as detected by sensor systems 103, 104. Resting and sleep phases L are detected by the processor(s) 13, 30, 40 using physiological parameters Y; particularly, heart rate H, heart rate variability V, and acceleration. Different sleep phases are determined by combining the measurements of the heart rate variability V and acceleration as described by Renevey et al. cited above.

In FIG. 2, reference numeral Y refers to the physiological parameters, at least some of which are measured and taken into consideration for monitoring and detecting the change in estrogen level E of the female human. Specifically, the physiological parameters Y include perfusion P, bio-impedance b (galvanic skin response, sweating, skin hydration s), heart rate H, heart rate variability V, breathing rate R, blood pressure B, sleep parameters L, and/or temperature T (body, wrist, skin temperature) of the female human.

Specifically, in step S1, a first sensor system of the wearable device 1, the perfusion sensor system 101, measures the (skin) perfusion P of the female user. More specifically, in the state of the device 1 being worn, e.g. on the wrist, the processor 13 of the wearable device 1 reads or receives from the perfusion sensor system 101 the currently measured (skin) perfusion P of the female user. In step S1, a second sensor system of the wearable device 1 measures further physiological parameters Y of the female user, as will be described later in more detail.

As indicated by reference numeral A, in an embodiment, behavioral parameters A of the female user are determined by the wearable device 1, at least some of which are taken into consideration for detecting the change in estrogen level E of the female human.

Specifically, the behavioral parameters A include activity level, number of social interactions, communication style, type of contacts, and/or number of intercourses. Depending on their specific type, the behavioral parameters A are determined by a sensor system of the wearable device 1 and/or by the processor 13 of the wearable device 1.

In step S2, the processor 13 stores the perfusion P (value) in the data store 12 together with a time stamp, including the current time and date. In step S2, the processor 13 stores further or other physiological parameters Y of the female user with time stamps, as will be described later in more detail. Depending on the embodiment and/or device configuration, in step S2, the processor 13 further stores further behavioral parameters A of the female user with time stamps.

As indicated by reference numeral D, the detected and stored perfusion P, further or other physiological parameters Y, behavioral parameters A, and their associated time stamps define the temporal course of one or more physiological and behavioral parameters Y, A of the female user.

Figure 3:
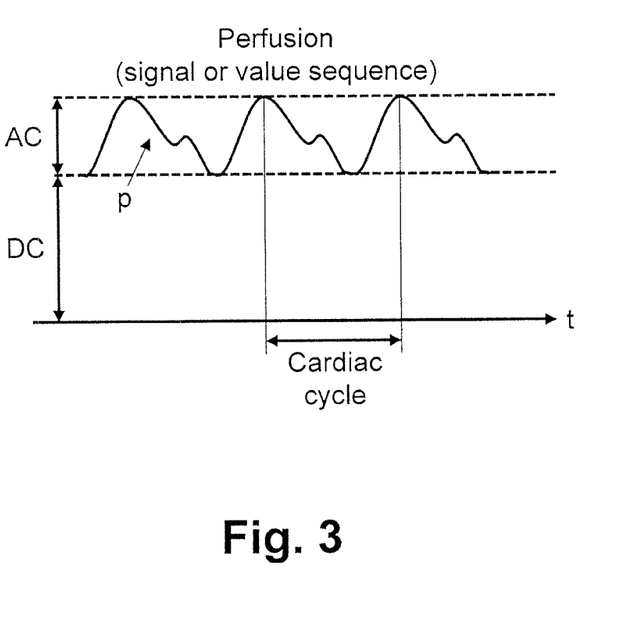
FIG. 3: shows a graph illustrating schematically AC and DC components of perfusion of a female human over the course of several cardiac cycles.

Either in step S1 or in step S2, the perfusion sensor system 101 or the processor 13, 30, 40 of the wearable device, computer system 3 or mobile communication device 4, respectively, normalizes the measured perfusion P by dividing the AC-component AC of the measured perfusion (signal or value sequence) p by the DC-component DC of the measured perfusion (signal or value sequence) p, as illustrated in FIG. 3, to obtain a normalized perfusion index.

In step S3, the (normalized) perfusion P and/or other physiologic parameters Y (as well as behavioral parameters A, if applicable) of the female user are processed to monitor and detect a change in estrogen level E of the female user during the menstrual cycle of the female user. Depending on the embodiment and/or configuration, the processing of the perfusion P and/or other physiologic parameters Y (as well as behavioral parameters A, if applicable) of the female user is performed by the processor 13 of the wearable device 1 and/or by the processor(s) 30, 40 of the computer system 3 and/or the mobile communication device 4. In the case, involving processing by the processor(s) 30 of the computer system 3, the measured and time stamped values of perfusion P and/or other physiological parameters Y (as well as behavioral parameters A, if applicable) are transmitted by the communication module 14 from the wearable device 1 via network 2 to the computer system 3, as indicated by step S4 in FIGS. 1a and 2, e.g. directly or via the mobile communication device 4 as a relay device. In the case, involving processing by the processor 40 of the mobile communication device 4, the measured and time stamped values of perfusion P and/or other physiological parameters Y (as well as behavioral parameters A, if applicable) are transmitted by the communication module 14 from the wearable device 1 via the close range communication interface to the mobile communication device 4 where they are stored in the data store 41. In the computer system 3 and/or the mobile communication device 4, respectively, the received measurement values and parameters are stored securely assigned to the female user, defined, for example, by a user identifier and/or a device identifier (for increased anonymity/privacy). Transmission of the time stamped measurements is performed periodically, for example; typically, the measurement and parameter data is transmitted less frequently than the measurements or detection are performed, e.g. various time stamped measurement and parameters, taken at different times, are grouped and transmitted together by the wearable device 1 in a combined data transmission.

Figure 4:
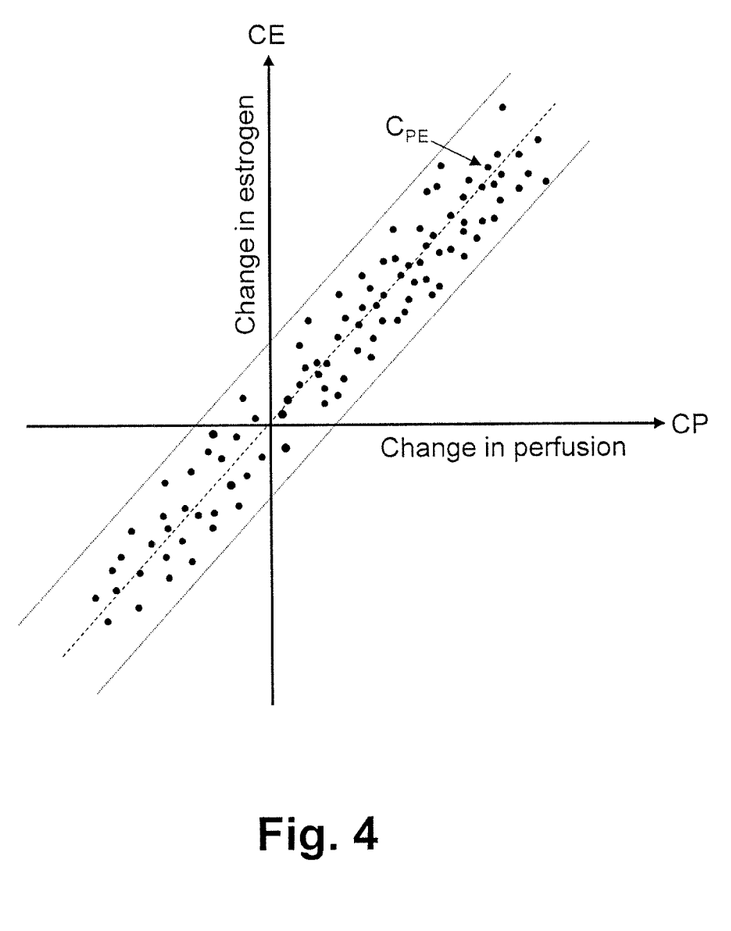
FIG. 4: shows a graph illustrating schematically the correlation of determined change in perfusion and change in estrogen levels for a plurality of points in time.
Figure 5:
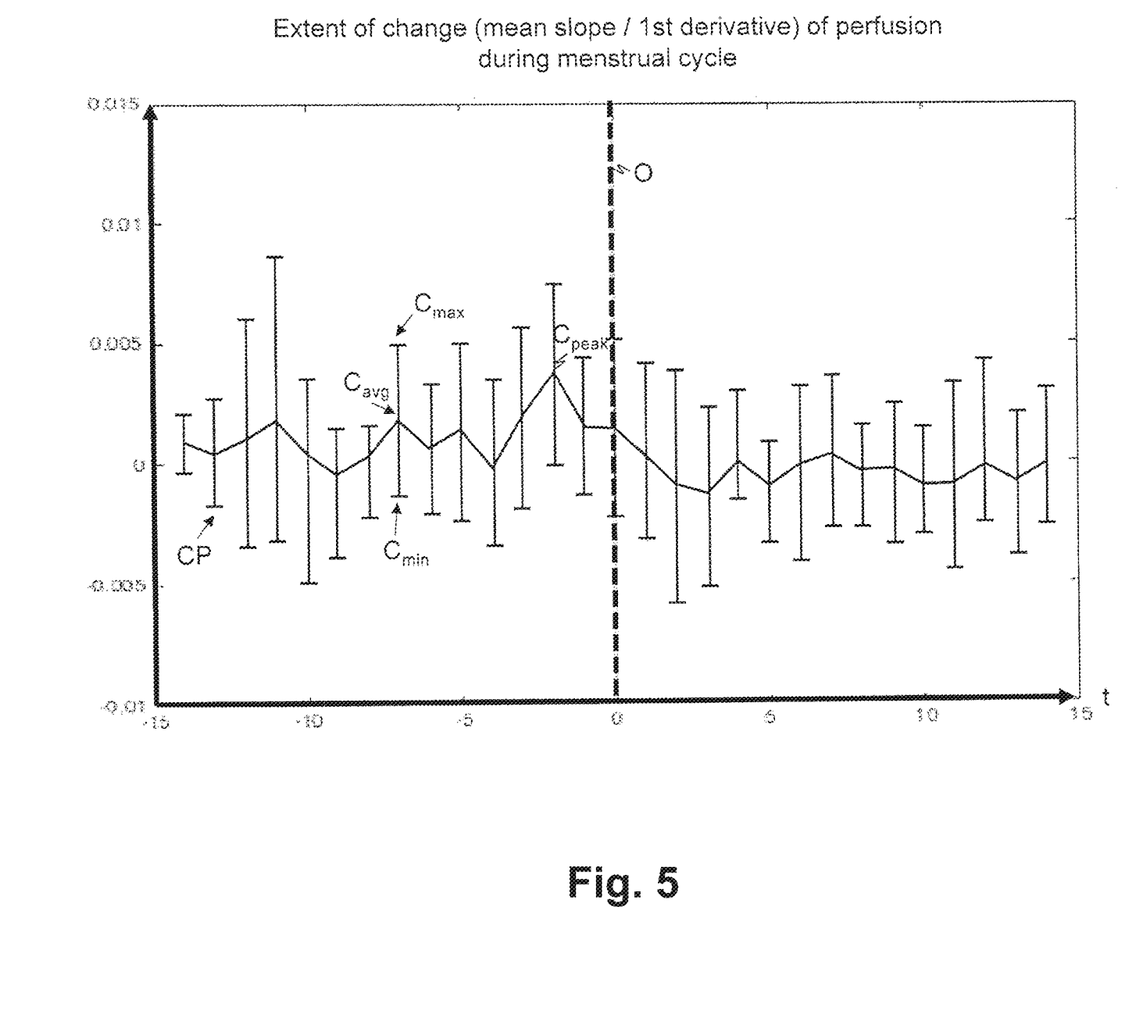
FIG. 5: shows a graph illustrating an example of the extent of change of perfusion of a female human over the course of a menstrual cycle.

Specifically, in step S3, the processor 13 of the wearable device and/or the processor(s) 30, 40 of the computer system 3 and/or the mobile communication device 4 determines from a plurality of measurements of the perfusion P the change in the level of perfusion P. The change of perfusion CP is detected from a plurality of (normalized) measurement points during the night (or during a detected sleeping phase), over one or more set time intervals, e.g. time intervals with a duration of a few minutes, e.g. one, two, five or ten minutes. In an embodiment, the change of perfusion CP is determined by calculating the first derivative (slope) of the temporal course of measured (and normalized) perfusion P. As illustrated in FIG. 5, for every night during the menstruation cycle of the female user, determined are the maximum extent of change $C_{max}$ of perfusion P, the minimum extent of change $C_{min}$ of perfusion P, and the average extent of change $C_{avg}$ of perfusion P. Based on the determined change of perfusion CP, the processor 13 of the wearable device and/or the processor(s) 30, 40 of the computer system 3 and/or the mobile communication device 4 determines the change of estrogen CE. In FIG. 4, every point $C_{PE}$ represents at a point in time (during the night) the change of perfusion CP and at the same point in time the change in the level of estrogen CE. As can be seen in FIG. 4, the change in perfusion CP correlates with the change in estrogen CE. Accordingly, if there is a detected/measured change in perfusion CP, there is a corresponding/correlating change in estrogen CE.

Figure 6:
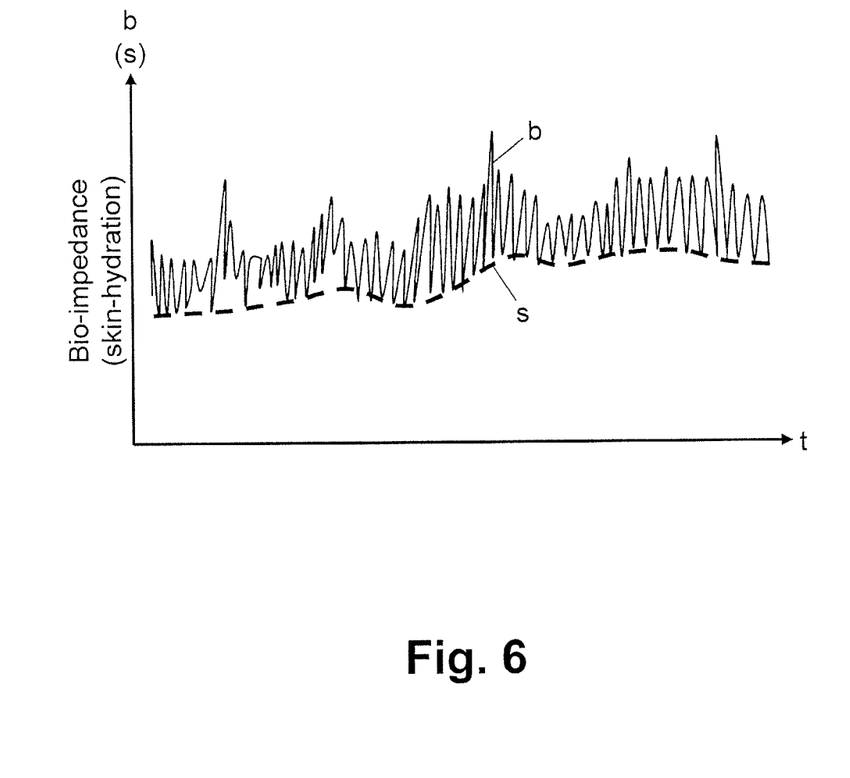
FIG. 6: shows a graph illustrating an example of the course and change of bio-impedance of a female human and the respective course and change of skin hydration derived from the bio-impedance.

Either in step S1 or in step S2, the processor 13 of the wearable device 1 and/or the processor(s) 30, 40 of the computer system 3 and/or the mobile communication device 4 determines from the measured and stored bio-impedance (skin-impedance) values, the skin hydration s of the female user. As illustrated in FIG. 6, the skin-hydration s is determined from the measured and recorded bio-impedance (signal or value sequence) b by determining the lower envelope of the bio-impedance (signal or value sequence) b.

In step S3, the bio-impedance b or skin-hydration s of the female user is processed to detect a change CE in estrogen level E of the female user during the menstrual cycle of the female user. Depending on the embodiment and/or configuration, the processing of the bio-impedance b or skin-hydrations of the female user is performed by the processor 13 of the wearable device 1 and/or by the processor(s) 30, 40 of the computer system 3 and/or the mobile communication device 4, as outlined above in connection with the perfusion P. Specifically, in step S3, the respective processor 13, 30, 40 determines from a plurality of measurements of the bio-impedance b or skin-hydration s the change in the level of bio-impedance b or skin-hydration s. The change of bio-impedance b or skin-hydration s is detected from a plurality of measurement points during the night (or during a detected sleeping phase). In an embodiment, the change of bio-impedance b or skin-hydration s is determined by calculating the first derivative (slope) of the temporal course of measured bio-impedance b or skin-hydration s. Based on the determined change of bio-impedance b or skin-hydration s, the processor 13 of the wearable device and/or the processor (s) 30, 40 of the computer system 3 and/or the mobile communication device 4 determines the change of estrogen E. As described above in connection with the change of perfusion CP with reference to FIG. 4, the change in bio-impedance b or skin-hydration s correlates with the change in estrogen E. Accordingly, if there is a detected/measured change in bio-impedance b or skin-hydration s, there is a corresponding/correlating change in estrogen E.

The determination of the change in estrogen CE based on the change in perfusion CP, based on the change of bio-impedance Cb or skin-hydration Cs, or based on other physiological parameters Y or behavioral parameters A, are used in combination (e.g. with weighted contribution of change in perfusion CP, change of bio-impedance Cb, change of skin-hydration Cs, or other physiological parameters Y or behavioral parameters A) or as alternatives. Below, Table 1 illustrates the relationship between various physiological parameters Y and behavioral parameters A and the level of estrogen.

TABLE 1

| Increase in physiological/behavioral parameter | Estimated estrogen level |
|---|---|
| Pulse rate | Lower |
| Breathing rate | Lower |
| Heart rate variability | Higher |
| Blood pressure | Lower |
| Bio-impedance | Lower |
| Perfusion | Higher |
| Social interaction level | Higher |
| Activity | Higher |
| Type of social communication and contacts | Individual |

A detected change of estrogen E level is indicated to the user on a user interface of the wearable device 1 or the mobile communication device 4 by the processor 13 or 40, respectively, e.g. on the display 16 as numerical value and/or a graphical representation indicating the extent of change. Depending on the embodiment, the detected change in estrogen E is transmitted by the processor(s) 30 of the computer system 3 via network 2 to the wearable device 1 and/or the mobile communication device 4. In an embodiment, the change of estrogen E level is indicated to the user, only if it exceeds a defined threshold, e.g. when the nightly average change of estrogen E level, as derived from the nightly average change $C_{avg}$ of perfusion P, exceeds a certain percentage, e.g. 20%. As explained below, the information about the change of estrogen E level is further used to inform the user about an upcoming ovulation.

In another embodiment, the highest change of estrogen E level, as derived from the highest average change $C_{peak}$ of perfusion P, is indicated to the user, as an indicator of the predicted time of ovulation O, which typically occurs two days after the highest change (strongest increase) of estrogen E level or the highest average change $C_{peak}$ of perfusion P, respectively, at night time during the menstruation cycle. In an embodiment, the processor 13 of the wearable device and/or the processor(s) 30, 40 of the computer system 3 and/or the mobile communication device 4 determines the predicted time of ovulation O of the female user, using the highest average change $C_{peak}$ of perfusion P, by adding an individual time lag (typically two days) to the time of the highest average change $C_{peak}$ of perfusion P. It should be noted that this time lag is individually different and is estimated based on analysis of recordings of previous (earlier) cycles for the respective female user.

In an embodiment, the processors 30 of the cloud-based computer system 3 are configured to implement an online user platform. The online user platform is configured to provide to authorized users secured access to their private personal data and stored measurement data.

It should be noted that, in the description, the computer program code has been associated with specific functional modules and the sequence of the steps has been presented in a specific order, one skilled in the art will understand, however, that the computer program code may be structured differently and that the order of at least some of the steps could be altered, without deviating from the scope of the invention.

The invention claimed is:

1. An electronic system for non-invasive monitoring of estrogen of a female human, the system comprising:
    a wearable device including a sensor system configured to be worn in contact with skin of the female human and to determine one or more physiological parameters of the female human; and
    a processor configured to receive and store the physiological parameters of the female human from the sensor system for a respective point in time;
    the processor being further configured to determine a change in the physiological parameters of the female human, using the physiological parameters of the female human stored for a plurality of respective points in time; and
    the processor being further configured to detect a change in estrogen level of the female human based on the change in the physiological parameters of the female human,
    wherein the sensor system is configured to determine a level of perfusion of the female human; and the processor is configured to receive and store the level of perfusion of the female human from the sensor system for a point in time, to determine a change in the level of perfusion of the female human, using the levels of perfusion of the female human stored for a plurality of points in time; and to detect the change in estrogen level of the female human based on the change in the level of perfusion of the female human.

2. The electronic system of claim 1, wherein the processor is configured to determine the change in the level of perfusion of the female human by calculating a first derivative of a course of the level of perfusion.

3. The electronic system of claim 1, wherein the processor is configured to determine the change in the level of perfusion of the female human by calculating a first derivative of a course of a perfusion index, the perfusion index being defined by an AC component of the level of perfusion normalized by a DC component of the level of perfusion.

4. The electronic system of claim 1, wherein the processor is configured to determine the change in the level of perfusion of the female human over one or more set time intervals during a resting phase of the female human.

5. The electronic system of claim 1, wherein the sensor system is configured to determine non-invasively the one or more physiological parameters of the female human, the one or more physiological parameters including at least one of: the level of perfusion, heart rate variability, heart rate, breathing rate, blood pressure, temperature, and bio-impedance.

6. The electronic system of claim 1, wherein the processor is configured to determine a resting phase of the female human using the one or more physiological parameters of the female human.

7. The electronic system of claim 1, wherein the processor is configured to receive and store one or more behavioral parameters of the female human from a mobile communication device, the one or more further behavioral parameters including at least one of: activity level, number of social interactions, number of intercourses, communication style, and type of contacts; and the processor is configured to detect the change in estrogen level of the female human, using the one or more behavioral parameters of the female human.

8. The electronic system of claim 1, wherein the processor is configured to determine a peak of the change in the level of perfusion of the female human during a menstrual cycle of the female human, and to determine a predicted time of ovulation of the female human, using the peak of the change in the level of perfusion.

9. The electronic system of claim 1, wherein the processor is arranged in the wearable device and configured to determine the change in estrogen level of the female human using the physiological parameters measured by the sensor system of the wearable device.

10. The electronic system of claim 1, wherein the processor is arranged in an external system, separated from the wearable device, the wearable device further comprises a communication module configured to transmit the physiological parameters measured by the sensor system of the wearable device to the external system, and the processor is configured to determine the change in estrogen level of the female human using the physiological parameters received from the wearable device.

11. A method of non-invasive monitoring of estrogen of a female human, the method comprising:
    receiving in a processor from a sensor system of a wearable device one or more physiological parameters of the female human for a respective point in time;
    storing, by the processor, the physiological parameters of the female human for the respective point in time;
    determining, by the processor, a change in the physiological parameters of the female human, using the physiological parameters of the female human stored for a plurality of respective points in time;
    detecting, by the processor, a change in estrogen level of the female human based on the change in the physiological parameters of the female human;
    determining, by the sensor system, a level of perfusion of the female human; and receiving and storing, by the processor, the level of perfusion of the female human from the sensor system for a point in time, to determine a change in the level of perfusion of the female human, using the levels of perfusion of the female human stored for a plurality of points in time, and to detect the change in estrogen level of the female human based on the change in the level of perfusion of the female human.

12. The method of claim 11, further comprising receiving in the processor from the sensor system of the wearable device the one or more physiological parameters of the female human including at least one of: the level of perfusion, heart rate variability, heart rate, breathing rate, blood pressure, temperature, and bio-impedance.

13. A computer program product comprising a non-transient computer readable medium having stored thereon computer program code configured to control one or more processors of a computerized system, such that the computerized system performs the steps of:
    receiving from a sensor system of a wearable device one or more physiological parameters of a female human for a respective point in time;
    storing the physiological parameters of the female human for the respective point in time;

determining a change in the physiological parameters of the female human, using the physiological parameters of the female human stored for a plurality of respective points in time;

detecting a change in estrogen level of the female human based on the change in the physiological parameters of the female human;

determining, by the sensor system, a level of perfusion of the female human; and receiving and storing, by the processor, the level of perfusion of the female human from the sensor system for a point in time, to determine a change in the level of perfusion of the female human, using the levels of perfusion of the female human stored for a plurality of points in time, and to detect the change in estrogen level of the female human based on the change in the level of perfusion of the female human.

14. The computer program product of claim 13, wherein the computer program code is further configured to control the one or more processors of the computerized system, such that the computerized system receives from the sensor system of the wearable device the one or more physiological parameters of the female human including at least one of: the level of perfusion, heart rate variability, heart rate, breathing rate, blood pressure, temperature, and bio-impedance.

* * * * *